(12) United States Patent
de Paz Sicam et al.

(10) Patent No.: US 9,743,832 B2
(45) Date of Patent: Aug. 29, 2017

(54) APPARATUS FOR CORNEAL SHAPE ANALYSIS AND METHOD FOR DETERMINING A CORNEAL THICKNESS

(71) Applicant: I-Optics B.V., 's-Gravenhage (NL)

(72) Inventors: Victor Arni de Paz Sicam, Rotterdam (NL); Roland Bryn Piper, The Hague (NL)

(73) Assignee: Cassini B.V., 'S-Gravenhage (NL)

( * ) Notice: Subject to any disclaimer, the term of this patent is extended or adjusted under 35 U.S.C. 154(b) by 349 days.

(21) Appl. No.: 14/663,004

(22) Filed: Mar. 19, 2015

(65) Prior Publication Data
US 2015/0190046 A1 Jul. 9, 2015

Related U.S. Application Data

(63) Continuation-in-part of application No. 12/937,816, filed as application No. PCT/EP2009/002977 on Apr. 16, 2009, now Pat. No. 9,004,689.

(30) Foreign Application Priority Data

Apr. 17, 2008 (EP) ..................... 08075303

(51) Int. Cl.
*A61B 3/10* (2006.01)
*A61B 3/107* (2006.01)
*A61B 90/30* (2016.01)

(52) U.S. Cl.
CPC .............. *A61B 3/107* (2013.01); *A61B 90/30* (2016.02); *A61B 2090/309* (2016.02)

(58) Field of Classification Search
CPC ......... A61B 3/102; A61B 3/14; A61B 3/0058; A61B 3/0008; A61B 3/1005; A61B 3/12
(Continued)

(56) References Cited

U.S. PATENT DOCUMENTS 5,054,907 A 10/1991 Sklar et al.
5,475,452 A 12/1995 Kuhn et al.
(Continued)

FOREIGN PATENT DOCUMENTS

EP 1632169 A2 3/2006
GB 1209451 A 10/1970

OTHER PUBLICATIONS

Jason Turuwhenua, Corneal Surface Reconstruction Algorithm Using Zernike Polynomial Representation: improvements, vol. 24, No. 6/Jun. 2007/J Opt. Soc. Am.A., 1551-1561.
(Continued)

*Primary Examiner* — Hung Dang
(74) *Attorney, Agent, or Firm* — Hoffman & Baron, LLP

(57) ABSTRACT

A method of determining a corneal thickness and an apparatus for determining the same. The method comprises the following steps of illuminating a cornea by a plurality of stimulator point light sources, capturing an image of the cornea comprising reflected images of the stimulator point light sources, obtaining a first model representing an anterior surface of the cornea, constructing a second model representing a posterior surface of the cornea from the image by ray-tracing the reflected images of the stimulator point light sources towards the first model representing the anterior surface of the cornea, and determining the corneal thickness from the first model representing the anterior surface and the second model representing the posterior surface.

28 Claims, 8 Drawing Sheets

(58) Field of Classification Search
USPC .............. 351/221, 211, 212, 246, 206, 205; 600/452, 558, 398, 399, 400, 401, 402, 600/403, 404, 405, 406; 250/559.27, 250/559.29; 356/125, 126; 606/5
See application file for complete search history.

(56) References Cited

U.S. PATENT DOCUMENTS

| | | | |
|---|---|---|---|
| 5,512,966 A * | 4/1996 | Snook | A61B 3/107 351/205 |
| 5,865,832 A | 2/1999 | Knopp et al. | |
| 5,867,250 A | 2/1999 | Baron | |
| 6,193,371 B1 | 2/2001 | Snook | |
| 6,692,126 B1 | 2/2004 | Xie et al. | |
| 7,252,380 B2 | 8/2007 | Koest | |
| 7,497,575 B2 | 3/2009 | Huang et al. | |
| 7,896,497 B2 | 3/2011 | McBeth | |
| 2004/0021826 A1 | 2/2004 | Sarver et al. | |
| 2005/0281440 A1 | 12/2005 | Permer | |
| 2011/0105943 A1 | 5/2011 | De Paz Sicam | |
| 2011/0273669 A1 | 11/2011 | Abitbol et al. | |

OTHER PUBLICATIONS

Helen Owens, PhD. et al., Posterior Corneal Changes with Orthokeratology, Optometry and Vision Science vol. 81, No. 6, Jun. 2004, 421-426.
Jason Turuwhenua, Ph.D., et al., The Recovery of Posterior Cornea and Anterior Lens Radii by a Novel Ray-Tracing Method, Optometry and Vision Science, vol. 81, No. 11, Nov. 2004.
International Search Report for PCT/EP2009/002977, mailed May 8, 2009.
Office Action issued on Mar. 18, 2013 with respect to U.S. Appl. No. 12/937,816.
Office Action issued on Aug. 26, 2013 with respect to U.S. Appl. No. 12/937,816.
Advisory Action issued on Dec. 6, 2013 with respect to U.S. Appl. No. 12/937,816.
Communication pursuant to Article 94(3) EPC for a counterpart foreign application, dated Jan. 11, 2017.

* cited by examiner

⟶ Path 1
-------≽ Path 2

APPARATUS FOR CORNEAL SHAPE ANALYSIS AND METHOD FOR DETERMINING A CORNEAL THICKNESS

CROSS-REFERENCE TO RELATED APPLICATIONS

This application claim priority benefit under 35 U.S.C. §120 as a Continuation-in-Part of prior non-provisional U.S. Utility patent application Ser. No. 12/937,816, filed 14 Oct. 2010, now U.S. Pat. No. 9,004,689, entitled APPARATUS FOR CORNEAL SHAPE ANALYSIS AND METHOD FOR DETERMINING A CORNEAL THICKNESS, which application in turn is the National Stage under 35 U.S.C. 371 of International Application No. PCT/EP2009/002977, filed Apr. 16, 2009, which claims the benefit of European Application No. EP 08075303.1, filed Apr. 17, 2008. The entire contents and disclosure of these related and/or priority applications are hereby incorporated by this reference herein for all purposes.

BACKGROUND OF THE DISCLOSURE

Determination of a corneal thickness is important for various diagnostic applications as well as an important part of various surgical interventions on the eye. A method and apparatus for obtaining such a thickness is e.g. known from U.S. Pat. No. 6,692,126. The apparatus disclosed applies a Placido ring illuminator to illuminate the cornea and derives a model of the anterior surface of the cornea from the image obtained. By projecting thin slits of light on the cornea, a second image can be taken and used to determine the corneal thickness from the model of the anterior surface and the second image.

The apparatus and method as known in the art suffers from a number of drawbacks. First of all, this system needs to focus on two different planes: firstly the iris plane for imaging the reflections of the Placido illuminator, and secondly the cornea plane for imaging the cornea, which is partially illuminated by the slits of light. This system therefore requires the use of two camera's or one camera with a rapidly moving lens. This will drive up complexity and costs of the camera.

Second, it is known that the use of a Placido ring illuminator requires some assumptions with respect to the corneal anterior surface. Due to the use of ring shaped light sources, a one-to-one correspondence between a point on the stimulator source (i.e. the Placido ring illuminator) and a point on the captured image cannot be determined unless certain symmetries in the corneal surface are assumed. As in reality, these assumed symmetries may not be present; inaccuracies may be introduced in the model. As the model is further on applied to determine the corneal thickness, inaccuracies in this thickness due to the assumed symmetries of the anterior surface may occur as well. It can further be noted that the use of slit-shaped illumination sources results in a similar problem in that a one to one correspondence between a point on the stimulator source (i.e. the slit-shaped illumination source) and a point on the captured image may be difficult to establish. A further drawback of the apparatus as known in the art is the requirement of sequentially capturing two images of the cornea to determine the corneal thickness. In case of a displacement of the eye between the capturing of the first and the second image, some uncertainty with respect to the position of the anterior surface of the cornea may exist when the second image is taken. This uncertainty may further introduce inaccuracies in the determination of the corneal thickness. As an alternative, it is proposed in U.S. Pat. No. 6,692,126 to use a camera system with multiple camera's each camera being arranged to record an image of one of the illumination sources. This may result in a more complex and therefore more expensive apparatus.

It is further acknowledged that other apparatuses exist for approximating a corneal thickness. One of such apparatuses is described in Optometry and Vision science, Vol. 67, No. 10, pp. 757-763 and uses a plurality of stimulator points for illuminating the cornea. The image obtained is used to estimate the corneal thickness by assuming that both the anterior surface and the posterior surface are spherical surfaces.

It is an object of the present disclosure to provide an apparatus for corneal diagnosis and a method for determining a corneal thickness that alleviates, at least partly, one or more of the drawbacks mentioned above.

SUMMARY OF THE DISCLOSURE

According to an aspect of the disclosure, there is provided a method of determining a corneal thickness comprising the steps of
  illuminating a cornea by a plurality of stimulator point light sources,
  capturing an image of the cornea comprising reflected images of the stimulator point light sources,
  obtaining a model representing an anterior surface of the cornea,
  constructing a second model representing a posterior surface of the cornea from the image by ray-tracing the reflected images of the stimulator point light sources towards the model representing the anterior surface of the cornea,
  determining the corneal thickness from the model representing the anterior surface and the second model representing the posterior surface.

Compared to the methods as known in the art, in the method according to the disclosure the construction of the posterior surface model is obtained by applying ray-tracing techniques to an image obtained by illuminating the cornea using a plurality of stimulator point light sources, rather than using slit-shaped illumination sources. Using ray-tracing techniques on an image obtained from stimulator point light sources facilitates the construction of the posterior surface model as it enables a one-to-one correspondence between a point on the stimulator source (i.e. the stimulator point light sources) and the reflected images of said light sources on the captured image. As such, no approximations or assumptions need to be made regarding the shape of the corneal surface. As a result, the method according to the disclosure enables a more accurate determination of the posterior surface compared to conventional methods. It can be noted that the method according to the present disclosure may e.g. apply an anterior surface model obtained from e.g. a conventional corneal topographer (e.g. a topographer designed for determining only shape of anterior cornea surface).

In a preferred embodiment of the method according to the disclosure, the model representing the anterior surface of the cornea is obtained by:
  capturing a corneal image obtained by illuminating the cornea with a stimulator source,
  using ray-tracing to determine a point of reflection of the stimulator source on the anterior surface, performing a fitting algorithm of the point of reflection to a mathematical model to obtain the model representing the anterior surface of the cornea.

It can be noted that the stimulator source may be of different types:

1) source that produces collimated beam,
2) general point source.

For the second case, ray tracing of the second Purkinje image does not necessarily coincide with the chief ray corresponding to the first Purkinje image. This means that if the anterior surface is well reconstructed using the first Purkinje images, the second Purkinje image is sufficient to reconstruct the posterior surface of the cornea. This provides for a simpler surface reconstruction compared to using slit sources because the complex correction for the combined effect of distortion and refraction is not necessary.

It can be noted that the corneal thickness as obtained can e.g. take the form of a table or array providing the corneal thickness at one or more points on the cornea. Said point or points can e.g. correspond to points on the anterior surface or the posterior surface. As such, the corneal thickness provides information on the distance between the anterior and posterior surface of the cornea at a number of points of the cornea. This information can e.g. be applied by a surgeon to determine which interventions to the eye are possible. Equally, the thickness can be presented as a function fitted to the corneal thickness as determined at a number of points.

According to another aspect of the disclosure, there is provided an apparatus for corneal shape analysis, the apparatus comprising a plurality of stimulator point light sources for, in use, illuminating a cornea of an eye,
a camera system for capturing reflected images of the stimulator point light sources,
a computational unit for, in use, performing the following steps
obtaining a model of an anterior surface of the cornea,
constructing a second model representing the posterior surface of the cornea by ray-tracing the reflected images of the stimulator point light sources towards the model representing the anterior surface of the cornea and
determining a corneal thickness from the model representing the anterior surface and the second model representing the posterior surface.

By applying ray-tracing techniques on an image comprising the reflected images of a plurality of stimulator point light sources to determine a model representing the posterior surface of a cornea, a more accurate model can be obtained compared the model obtained by using conventional apparatuses for corneal diagnosis.

It can further be noted that the apparatus according to the disclosure may equally be applied to determine a model of the anterior surface of the cornea, thereby eliminating either the requirement for a separate apparatus for obtaining said model or the requirement of an additional illumination source (e.g. a Placido ring illuminator) for determining said model.

In a preferred apparatus according to the disclosure, the camera system is arranged to capture a first image comprising reflected images of the stimulator point light sources and to capture a second image comprising reflected images of the stimulator point light sources, the computational unit further being arranged to, in use, obtain the model of an anterior surface of the cornea using the first image and construct the second model representing the posterior surface using the second image.

In accordance with the present disclosure, a computational unit may e.g. comprise a processor, microprocessor, computer or the like. Typically, such a computational unit may comprise an input terminal for receiving data to be processed, e.g. image data of a camera system and an output terminal for outputting processed data, e.g. a mathematical model of the cornea or the lens or the eye.

In a yet further embodiment of the apparatus according to the disclosure, the apparatus further comprises a control unit for setting an illumination level of the stimulator point light sources thereby enabling the first and second image to be captured with a different illumination level. As will be explained further, it may be advantageous to have a different illumination level for the first and second image, said images being used, in a preferred embodiment of the disclosure to construct the models of the anterior and posterior surfaces of the cornea.

According to a further aspect of the present disclosure, provided is a method of determining a model of a lens of an eye. The method comprises the steps of:

illuminating an eye by a plurality of stimulator point light sources;

capturing an image of the eye comprising reflected images of the stimulator point light sources, the reflected images including 3th and 4th Purkinje images;

obtaining a first model representing an anterior surface of a cornea of the eye;

obtaining a second model representing a posterior surface of the cornea of the eye; and constructing a third model representing a front surface of the lens of the eye from the image by ray-tracing the reflected images of the stimulator point light sources towards the stimulator point light sources via the first and second models representing the anterior and posterior surfaces of the cornea.

In a further aspect of the present disclosure, provided is an apparatus for eye analysis. The apparatus comprises:

a plurality of stimulator point light sources for, in use, illuminating an eye;

a camera system configured to capture reflected images of the stimulator point light sources, the reflected images including 3th and 4th Purkinje images; and a computational unit configured to, in use, perform the following steps:

obtaining a first model representing an anterior surface of the cornea of the eye;

obtaining a second model representing a posterior surface of the cornea of the eye; and constructing a third model representing a front surface of a lens of the eye from the image by ray-tracing the reflected images of the stimulator point light sources towards the stimulator point light sources via the first and second models representing the anterior and posterior surfaces of the cornea.

In still another aspect of the present disclosure, provided is a method of determining an optical model of an eye. The method comprises the steps of:

illuminating an eye by a plurality of stimulator point light sources;

capturing one or more images of the eye comprising reflected images of the stimulator point light sources, constructing a first model representing an anterior surface of the cornea of the eye by ray-tracing the reflected images of the stimulator point light sources towards the stimulator point light sources, the reflected images including 1st Purkinje images of the stimulator point light sources;

constructing a second model representing a posterior surface of the cornea by ray-tracing the reflected images of the stimulator point light sources via the first model representing the anterior surface of the cornea, towards the stimulator point light sources, the reflected images including 2nd Purkinje images of the stimulator point light sources;

constructing a third model representing a front surface of the lens of the eye by ray-tracing the reflected images of the stimulator point light sources towards the stimulator point light sources via the first and second models representing the anterior and posterior surfaces of the cornea, the reflected images including 3th Purkinje images of the stimulator point light sources;

constructing a fourth model representing a back surface of the lens of the eye by ray-tracing the reflected images of the stimulator point light sources towards the stimulator point light sources via the first and second models representing the anterior and posterior surfaces of the cornea and the third model representing the front surface of the lens, the reflected images including 4th Purkinje images of the stimulator point light sources;

determining a central corneal thickness based on the first and second models;

determining a thickness of the lens of the eye based on the third and fourth models; and determining an anterior chamber depth.

In a still further aspect of the present disclosure, provided is an apparatus for eye analysis. The apparatus comprises:

a plurality of stimulator point light sources for, in use, illuminating an eye;

a camera system configured to capture one or more images of the eye comprising reflected images of the stimulator point light sources; and a computational unit configured to, in use, perform the following steps:

constructing a first model representing an anterior surface of the cornea of the eye by ray-tracing the reflected images of the stimulator point light sources towards the stimulator point light sources, the reflected images including 1st Purkinje images of the stimulator point light sources;

constructing a second model representing a posterior surface of the cornea by ray-tracing the reflected images of the stimulator point light sources via the first model representing the anterior surface of the cornea, towards the stimulator point light sources, the reflected images including 2nd Purkinje images of the stimulator point light sources;

constructing a third model representing a front surface of the lens of the eye by ray-tracing the reflected images of the stimulator point light sources towards the stimulator point light sources via the first and second models representing the anterior and posterior surfaces of the cornea, the reflected images including 3th Purkinje images of the stimulator point light sources;

constructing a fourth model representing a back surface of the lens of the eye by ray-tracing the reflected images of the stimulator point light sources towards the stimulator point light sources via the first and second models representing the anterior and posterior surfaces of the cornea and the third model representing the front surface of the lens, the reflected images including 4th Purkinje images of the stimulator point light sources;

determining a central corneal thickness based on the first and second model;

determining a thickness of the lens of the eye based on the third and fourth model and;

determining an anterior chamber depth of the eye.

BRIEF DESCRIPTION OF THE FIGURES

These and other features, aspect, purposes, goals and advantages of the present disclosure will become apparent from the following detailed description of example embodiments read in connection with the accompanying drawings, in which like reference numerals refer to like structures across the several views. The accompanying figures are offered only by way of example and without limiting the broad scope or various other embodiments of the present invention.

DETAILED DESCRIPTION OF THE DISCLOSURE

Figure 1:
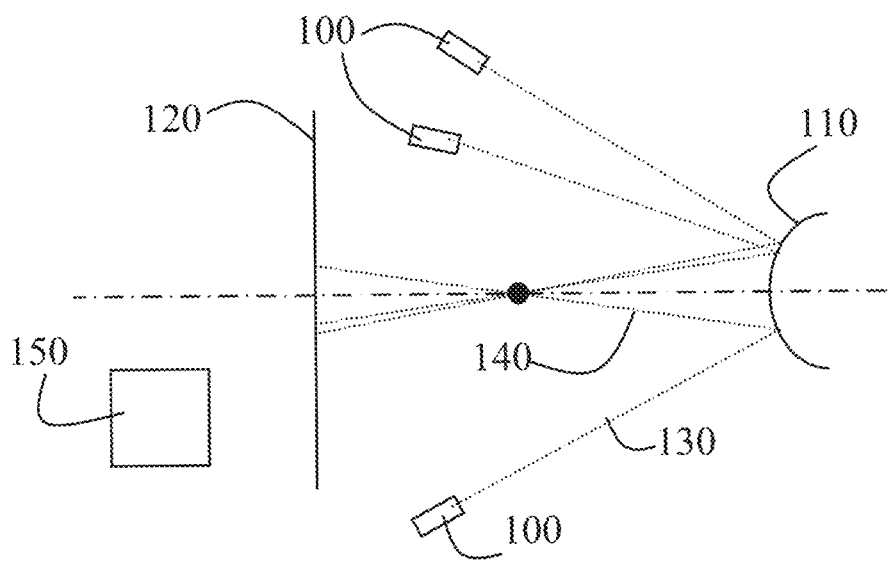
FIG. 1 schematically depicts a first embodiment of an apparatus for corneal diagnosis according to the disclosure.

FIG. 1 schematically depicts a first embodiment of an apparatus for corneal diagnosis according to the disclosure. The apparatus comprises a plurality of stimulator point light sources 100 arranged to, in use, illuminate a cornea of an eye. Contour 110 schematically represent the anterior surface of the cornea. The apparatus further comprises a camera system 120 arranged to capture an image of the reflections of the stimulator point light sources on the cornea. FIG. 1 further schematically depicts rays of light 130 originating from the plurality of stimulator point light sources and directed towards the cornea and the corresponding reflected rays 140 on the anterior surface 110 of the cornea. The apparatus as shown in FIG. 1 further comprises a computation unit 150 arranged to process an image obtained from the camera system in such manner that a corneal thickness is obtained.

In accordance with the present disclosure, a computational unit 150 may e.g. comprise a processor, microprocessor, computer or the like. Typically, such a computational unit may comprise an input terminal for receiving data to be processed, e.g. image data of a camera system such as the camera system 120 and an output terminal for outputting processed data, e.g. a mathematical model of the cornea or the lens or the eye.

In an embodiment of the present disclosure, the computational unit 150 is arranged to perform the following steps:

1. obtaining a model of an anterior surface of the cornea,
2. constructing a second model representing the posterior surface of the cornea by ray-tracing the reflected images of the stimulator points towards the model representing the anterior surface of the cornea and
3. determining the corneal thickness from the model representing the anterior surface and the reconstructed posterior surface.

In order to perform step 1, as an example, the computational unit can be arranged to receive a model representing the anterior surface. Said model can e.g. be obtained by analysing the anterior surface of the cornea with a conventional corneal topographer. Such a topographer can e.g. apply a Placido ring illuminator as a stimulator source for illuminating the cornea. Such a model can e.g. take the form of a mathematical model describing the anterior surface. Examples of such mathematical models are spherical models, models using spline functions or Zernike polynomials.

In a preferred embodiment, step 1 is preceded by a step of determining the centre of gravity of all reflected light sources.

Once the model of the anterior surface is obtained, the computational unit of the apparatus according to an embodiment of the disclosure can use the model representing the anterior surface together with a captured image of the reflections of the stimulator point light sources, to determine a model of the posterior surface of the cornea by using ray-tracing techniques. Examples of ray-tracing methods as applied in the present disclosure are described further on. The model of the posterior surface may equally take the form of a mathematical model similar to the anterior surface model. Once both the anterior surface and the posterior surface model are established, the corneal thickness can be determined. Starting from either the anterior surface or the posterior surface, the smallest distance towards the other of the two surfaces can be determined for each point of interest, said smallest distance corresponding to the corneal thickness at said point.

In the apparatus according the disclosure, the cornea is illuminated by stimulator point light sources. Contrary to known light sources such as Placido ring illuminators or slit-lamp illuminators, stimulator point light sources cause a reflection of a single spot only instead of a region (such as a ring or slit). As a consequence, a one to one correspondence between the illumination light source coordinates and the coordinates of the image of said light source as captured by the camera system can easily be established. This is important as it enables a more accurate ray-tracing between the illumination source and the captured image.

Instead of obtaining the model representing the anterior surface from e.g. a corneal analysis using a conventional topographer, the apparatus according to the disclosure may be applied to determine the anterior surface model, using the stimulator point light sources. In this case, the anterior surface model can e.g. be obtained from the same image as used to determine the posterior surface model thereby eliminating any uncertainty with respect to the position of the eye.

As an alternative, two different images can be taken by the camera system of the apparatus according to an embodiment of the disclosure, one image for obtaining the model of the corneal surface, and another one for determining the model representing the posterior surface. The images can advantageously be formed using different illumination levels. In a preferred embodiment, the apparatus according to the disclosure may therefore comprise a control unit for determining the illumination level of the stimulation point light sources. In a preferred embodiment, such a control unit may further be arranged to selectively enable the stimulator point light sources. As such, a first sub set of the stimulator point light sources can e.g. be selected and applied to generate a first image at a predetermined illumination level, said image being used to generate a model representing the anterior surface. Thereafter, a second image can be generated by e.g. illuminating the cornea with either the same or a different sub set of stimulator point light sources (e.g. at a different illumination level), said image being used to determine a second model representing the posterior surface of the cornea. The control unit as applied in a preferred embodiment of the apparatus according to the disclosure may equally be applied to control the duration of the illumination. As such, the apparatus according to the disclosure can be arranged to (very) briefly set an illumination level for a part of the stimulator's light sources in order to generate a first image optimized for detecting the shape of the anterior cornea, and secondly for selecting and setting an different but equally brief illumination level for a part of the stimulator's light sources in order to generate a second image optimized for detecting the shape of the posterior cornea. As the eye position may change between the capturing of the two images, the preferred apparatus according to the disclosure may therefore comprise a camera system for capturing in rapid succession two reflected images of the stimulator point light sources,
a computational unit for, in use, performing the following additional step
verifying whether a substantial eye movement has occurred based on comparing and analyzing the position of the iris in both images, Contrary to the prior art, in a preferred embodiment of the present disclosure, it is possible to use a one camera system with a fixed lens—the camera system being arranged such that a focal plane substantially corresponds to the iris plane for determining the shape of both surfaces.

In a preferred embodiment, the stimulator point light sources may comprise sources projecting beams which are constricted in size and aimed at the pupil in order to substantially avoid illuminating the iris, therewith increasing contrast between $2^{nd}$ Purkinje images and iris.

In a preferred embodiment of the apparatus according to the present disclosure, the stimulator point light sources comprise one or more LED light sources. The brightness and illumination duration of such LED sources are easily controllable. In addition, LEDs can, due to their size, advantageously be applied to provide a large multitude of stimulator point light sources.

As an alternative, laser diodes or conventional light sources with point-like apertures can be applied to provide light beams to illuminate the cornea.

It can further be noted that a single light source can be used to generate the plurality of stimulator point light sources. As an example, optical fibres and beam splitting techniques can be applied to provide multiple stimulator point light sources originating from a single light source such as a LED, a laser diode or a collimated light source.

Figure 2:
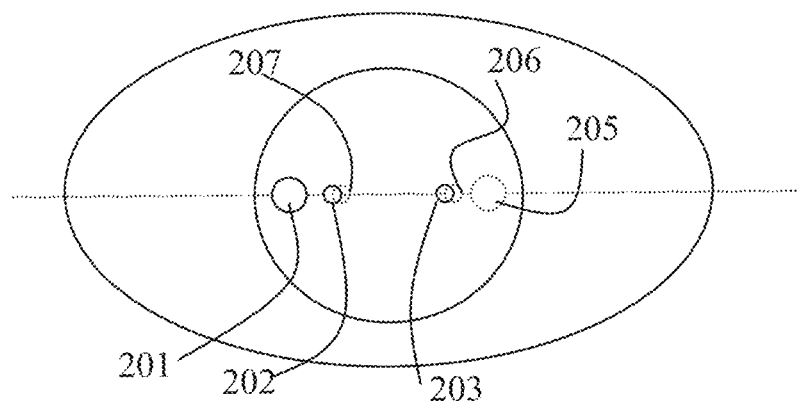
FIG. 2 schematically depicts first, second and fourth Purkinje images originating from two diametrically opposed stimulator point light sources.
Figure 3:
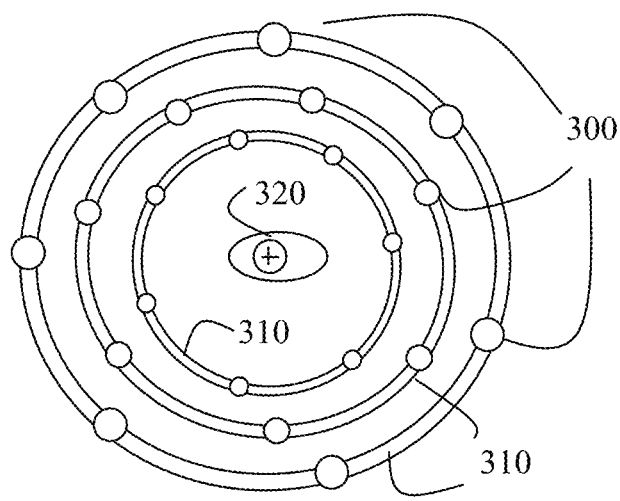
FIG. 3 schematically depicts an arrangement of the stimulator point light sources of an apparatus for corneal diagnosis according to the disclosure.

In a preferred embodiment of the present disclosure, the plurality of stimulator point light sources are located on one or more concentric circles, said circles being arranged such that the distance towards the cornea of the stimulator point light sources on a circle is the same for all sources. Such an arrangement facilitates the determination of the model of the posterior surface. In a yet further preferred embodiment, diagonals that can be constructed from the various stimulator point light sources do not coincide. As will be appreciated by the person skilled in the art, when a cornea is illuminated by a stimulator point light source, four reflections (known as Purkinje images) can occur: two reflections occurring at the cornea (resulting in first and second Purkinje images) and two reflections at the lens (resulting in third and fourth Purkinje images). As the fourth Purkinje image is an inverted image, said image generated by a first stimulator point light source may interfere with a first or second Purkinje image of a second stimulator point light source that is diametrically opposed to the first light source. To illustrate this, FIG. 2 schematically depicts the first, second and fourth Purkinje images from two diametrically opposed stimulator point light sources. In FIG. 2, reference numbers 201, 202 and 203 refer to the first, second and fourth Purkinje image of a first light source (not shown), reference numbers 205, 206 and 207 refer to the first, second and fourth Purkinje image of a second light source (not shown). As can be seen, the second and fourth Purkinje images somewhat overlap. As a consequence, it may be cumbersome to exactly locate the coordinates of the second Purkinje image, said image corresponding to the virtual image of the posterior surface of the cornea. By ensuring that the stimulator point light sources are not diametrically opposed, one can substantially reduce interference or overlap between the different Purkinje mages. A possible arrangement of the stimulator point light sources is illustrated in FIG. 3. FIG. 3 schematically depicts 21 stimulator point light sources 300 arranged on three ring shaped holders 310 that are concentrically arranged about an eye 320. The various stimulator point light sources are arranged in such manner that no light sources are diametrically opposed. One way of achieving this to ensure that each circle comprises an evenly distributed odd number of stimulator point light sources. By doing so, interference or overlap of the different Purkinje images can be mitigated or avoided.

A further factor important in establishing a model of either the anterior surface or the posterior surface is the brightness of the reflected images. In this respect, it can be noted that there is a substantial difference in brightness between the first Purkinje image (i.e. the reflection at the anterior surface of the cornea) and the second Purkinje image, the reflection at the posterior surface of the cornea. It can e.g. be observed that the brightness of the first Purkinje image can be approximately at least 100 times higher than the brightness of the second Purkinje image. Therefore, in order to accurately observe the second Purkinje image, the intensity of the stimulator point light sources should be made sufficiently high.

In order to facilitate determining the coordinates of the reflected images of the stimulator point light sources, it is preferred that the contrast between the reflected image and the background is as large as possible. One way to achieve this is to ensure that the orientation and beam width of the rays from each stimulator point light source is such that the iris of the eye is not or barely illuminated. As such, reflections from the iris can be mitigated or avoided thereby improving the contrast of the reflections on the image. As an alternative, the pupil could be dilated prior to the capturing of an image or images, thereby increasing the pupil, which provides a dark background and therefore a good contrast for determining locations of the second Purkinje images.

As already mentioned above, the apparatus according to the disclosure may equally be applied to derive a model for the anterior surface. In order to obtain such model representing the anterior surface, there is no need to observe the second Purkinje image as it represents a reflection of the posterior surface. In such a situation, it may be advantageous to apply a reduced intensity of the stimulator point light sources. This is illustrated in the following FIG. 4.

In case the corneal surface of an eye is illuminated by a stimulator point light source, the reflected image as received by the camera system may look like a spot of a certain diameter (e.g. due to optical aberrations and non-zero size of point source). In order to determine a model of the anterior surface as accurately as possible, the coordinates of the intersection of the ray of light originating from the stimulator point light source with the anterior surface should be determined as accurately as possible. This intersection point can be derived using the location of the captured first Purkinje image spot on the camera. When the pixels in this spot are substantially overfilled (many pixels will have the maximum grey level), the spot appears on the image as a spot with a substantially uniform brightness, taking the coordinates of the centroid of the spot as the required coordinates would actually be the only available option. When the image is made with a reduced intensity however, (as would be acceptable since the reflections on the posterior surface need not be determined) the spot may appear as having a varying intensity over its area. In such a situation, the required coordinates can be determined as the position having the highest intensity, thereby providing a more accurate position of the point of intersection of the ray of light originating of the stimulator point light source with the anterior surface.

Figure 4:
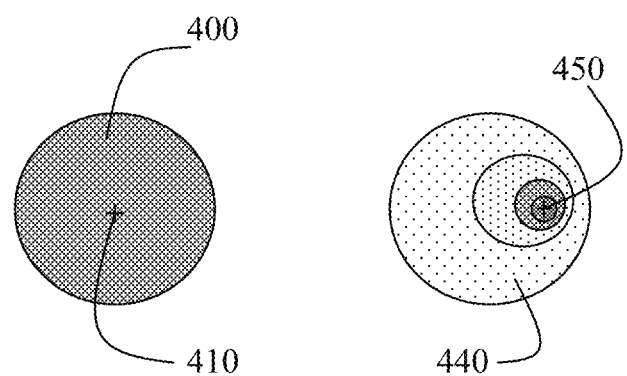
FIG. 4 schematically depicts a reflected image of a stimulator point light source at a high intensity value and at a low intensity value.

FIG. 4 therefore schematically depicts on the left a spot 400 of certain size having a uniform intensity (or brightness) together with the estimated intersection point 410 (i.e. the centre point of the spot). On the right, an image of a similar spot 440, obtained by illuminating the cornea with a reduced intensity, said spot having a varying intensity over its area (indicated by the different patterns). Indicated by 450 is the selected intersection point as the point having the highest intensity. As can be noticed, by capturing an image of reduced intensity, a more accurate determination of the location of the Purkinje image on the camera can be made leading to an accurate calculation of the intersection. It will be appreciated by the skilled person that a more accurate determination of the coordinates of the intersection of the ray of light originating of the stimulator point light source with the anterior surface can result in a more accurate model of the anterior surface. As the determination of the model of the posterior surface relies on the model of the anterior surface, the accuracy of the anterior surface model will affect the accuracy of the posterior surface model and consequently also the accuracy of the corneal thickness.

Figure 5:
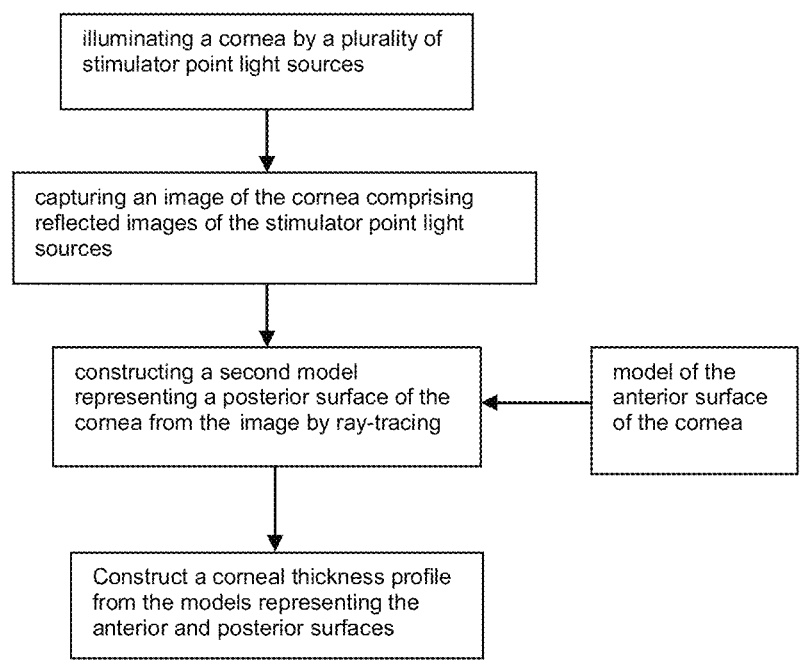
FIG. 5 schematically depicts a flow chart of an embodiment of the method according to the present disclosure.

As already mentioned, the present disclosure provides in a method for determining a corneal thickness. FIG. 5 schematically describes a flow chart of an embodiment of the method according to the present disclosure. In a first step, a cornea is illuminated by a plurality of stimulator point light sources. In a next step, an image of the cornea comprising reflected images of the stimulator point light sources is captured, e.g. by a CCD camera. In the method according to the disclosure, the captured image is used to determine a model of the posterior corneal surface using a model of the anterior surface combined with ray-tracing techniques. The anterior surface model can be obtained from either a separate measurement using a corneal topographer or can be obtained using the apparatus according to the disclosure. The latter case may provide additional advantages as it enables the model representing the anterior surface to be more accurate compared to a model obtained from a conventional Placido based topographer. As will be appreciated by the skilled person, a more accurate model of the anterior surface can enable the posterior corneal surface to be determined with a higher accuracy.

As an example on how a model can be obtained representing the anterior surface of the cornea, reference can be made to the J. Opt. Soc. Am. A/Vol. 21, No. 7/July 2004, "Corneal surface reconstruction algorithm that uses Zernike polynomial representation".

In general, the reflections of a stimulator source on the anterior corneal surface are detected from an image taken by the camera system. From the geometry of the apparatus, the known geometry of the stimulator source and the observed reflections, the corneal apex point can be determined. This point is used as a reference point for reconstructing the corneal surfaces. Once the apex point is determined, any suitable mathematical model can be referenced to this reference point and used to model the anterior surface. Several options exist for modelling either the anterior or the posterior surface.

As an example, a toric aspheric model can be applied. In cylindrical coordinates $\rho,\theta,z$, the model can be described as:

$$z^2 - 2rz + k\rho^2 = 0$$

$$r = r_0 - \delta r \cos^2(\theta - \alpha) \quad (1)$$

Where k is the asphericity, r is the meridian radius of curvature, $r_0$ is the maximum radius of curvature, $\delta r$ is the toricity and $\alpha$ is the axis of astigmatism.

A polynomial series expansion (i.e. Zernike, Taylor) is another example on how to model the corneal surfaces.

The parameters of the mathematical model can be determined from the known geometry of the apparatus and the reflected images of the stimulator source. When stimulator point light sources are applied, ray tracing can be applied to determine the parameters of the mathematical model. This can be done using the following conditions:

the ray of light originating from the stimulator point light source and the reflected ray towards the camera system need to fulfil the law of specular reflection; the angle of the anterior surface normal with the incident ray (ray originating from the stimulator source) should be equal to the angle between the anterior surface normal and the reflected ray.

the intersection point of the incident ray and the reflected ray is a point on the anterior surface.

The principle as described can be applied for each of the plurality stimulator point light sources thereby obtaining the coordinates of a plurality of points on the anterior surface of the cornea. A least squares fitting can then be done using the mathematical model and the reflection restrictions to determine the exact points of reflection on the anterior corneal surface. As a result, a model of the anterior corneal surface in terms of asphericity (k-value) and toricity (maximum radius, minimum radius and axis) can be obtained.

It can be noted that by analysing the stimulator point light source reflections by algorithms based on ray tracing as described above, a more accurate model is obtained compared to known algorithms based on paraxial analysis. In principle, paraxial analysis is an approximation using spherical model of the cornea. Ray tracing methods for an asphericity of k=0.47 for the anterior surface describe a surface that will give exactly the same results as the paraxial model. Other asphericity values will lead to different results. The average corneal asphericity is 0.9 and therefore the paraxial model is not enough.

Once a model for the anterior surface is obtained, a model for the posterior surface can be determined using ray-tracing techniques. An example of ray-tracing techniques as applied in the present disclosure is illustrated in FIG. 6.

Figure 6:
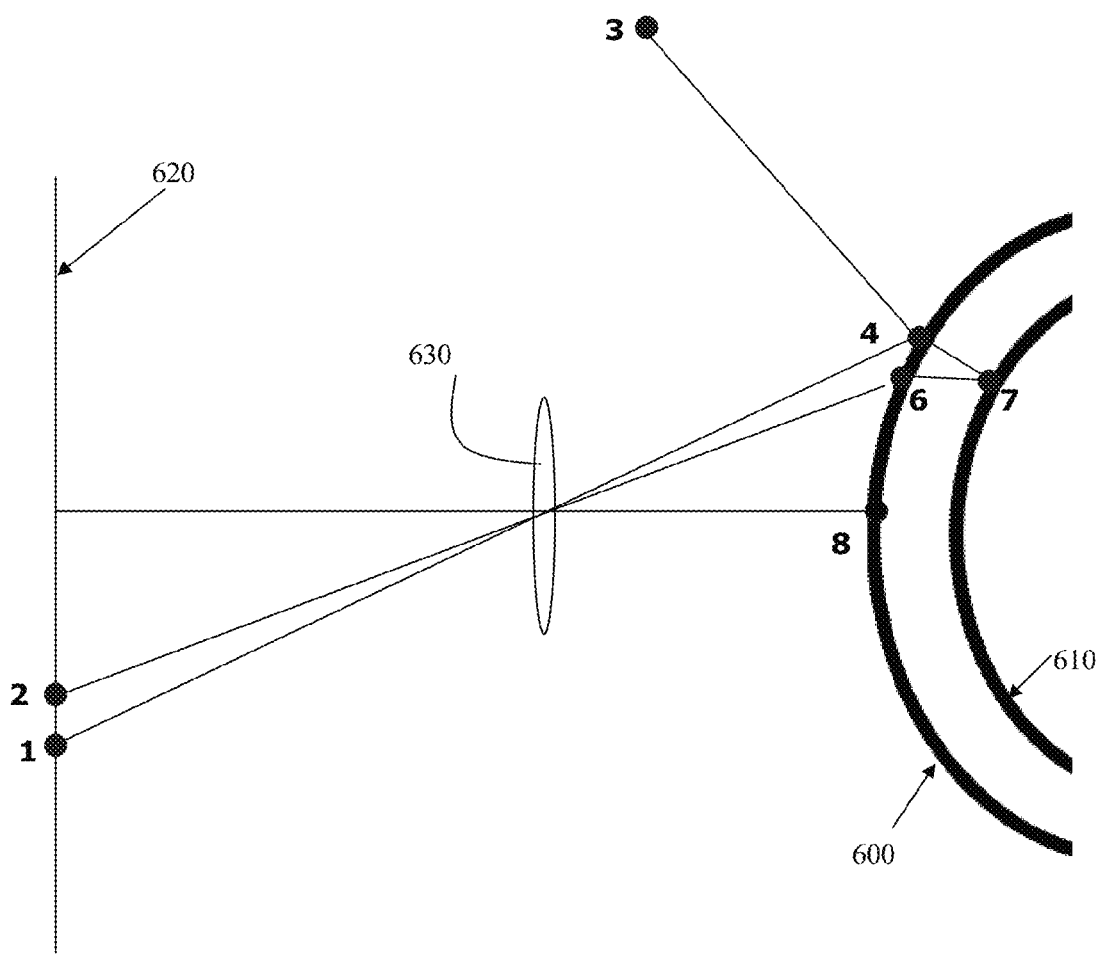
FIG. 6 schematically illustrates an embodiment of the use of ray-tracing to obtain a model of the posterior surface of the cornea as applied in the present disclosure.

FIG. 6 schematically depicts the anterior 600 and posterior 610 surfaces of a cornea, a stimulator point light source 3, a ray of light 3-4 originating from a stimulator point light source and the reflected rays of said ray of light on both the anterior and posterior surface, said reflected rays being captured by a camera system 620. FIG. 6 further shows a lens 630 representing a nodal point of the camera system.

The coordinates of a point on the posterior surface can be determined by the following steps:

constructing a first ray 1-4 originating from the first Purkinje image 1 of the stimulator point light source 3 towards the cornea, determining a first intersection point 4 as the intersection of the first ray with the model representing the anterior surface.

construct a second ray 2-6 originating from the second Purkinje image 2 of the stimulator point 3 towards the cornea, determining a second intersection point 6 as the intersection of the second ray with the model representing the anterior cornea, constructing a first refracted ray 4-7 from the first ray into the cornea originating from the first intersection point, using Snell's Law and the model representing the anterior cornea, constructing a second refracted ray 6-7 from the second ray into the cornea originating from the second intersection point, using Snell's Law and the model representing the anterior cornea, determine a point on the posterior surface as the intersection of the first and second refracted ray.

Note that the refracted ray 4-7 may equally be determined from the refraction of the ray originating from the stimulator point light source 3-4. The coordinates of a point on the posterior surface can then be determined by the following steps:

constructing a first ray 3-4 originating from the stimulator point light source 3 towards the cornea, determining a first intersection point 4 as the intersection of the first ray with the model representing the anterior surface.

construct a second ray 2-6 originating from the second Purkinje image 2 of the stimulator point 3 towards the cornea, determining a second intersection point 6 as the intersection of the second ray with the model representing the anterior cornea, constructing a first refracted ray 4-7 from the first ray into the cornea originating from the first intersection point, using Snell's Law, constructing a second refracted ray 6-7 from the second ray into the cornea originating from the second intersection point, using Snell's Law, determine a point on the posterior surface as the intersection of the first and second refracted ray.

Figure 7:
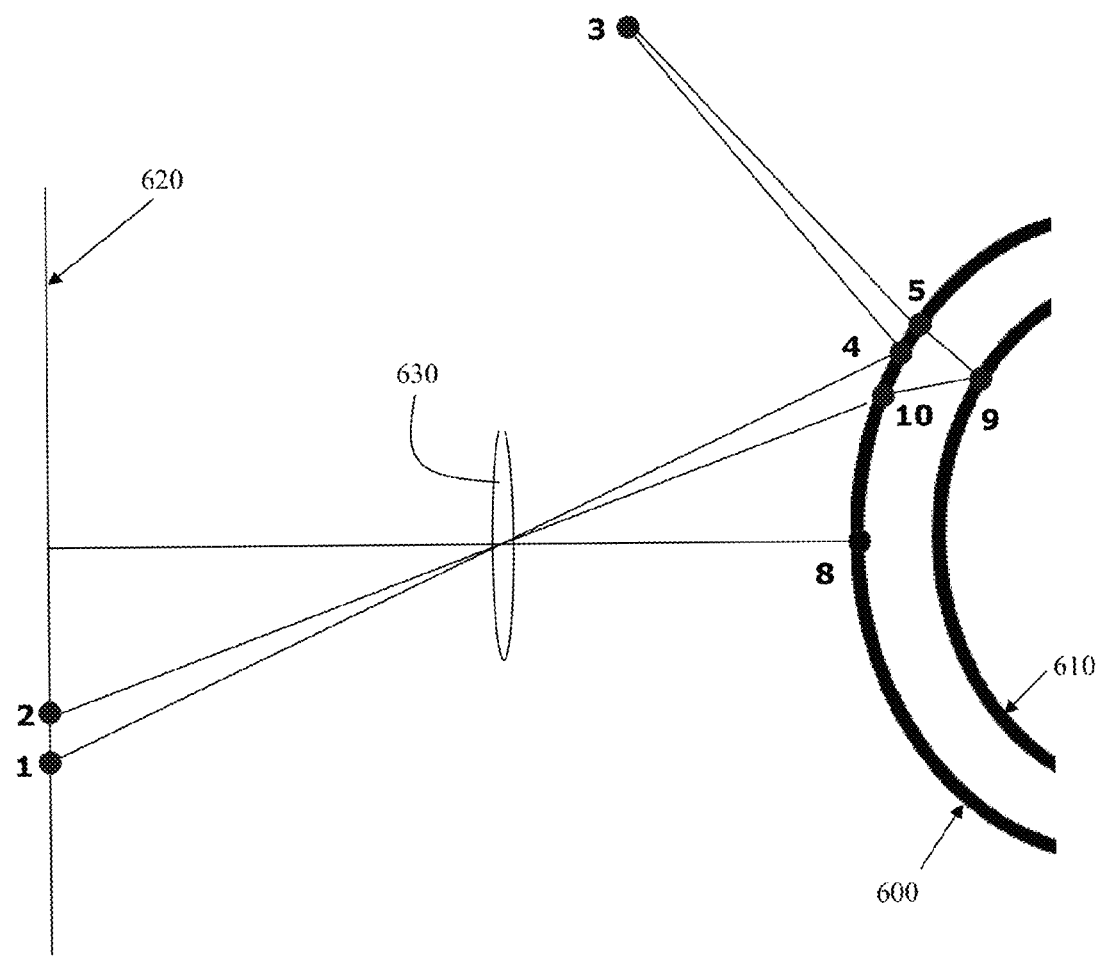
FIG. 7 schematically illustrates a preferred embodiment of the use of ray-tracing to obtain a model of the posterior surface of the cornea as applied in the present disclosure.

FIG. 6 illustrates ray tracing corresponding to a source producing a collimated beam. If the light source does not produce a collimated beam, the chief ray for the $2^{nd}$ Purkinje image may take a different path as illustrated in FIG. 7 (Path 3-5-9-10-2). The same reference number in FIG. 6 for the traced path of the first Purkinje image 1 is used. In this case, the construction of the posterior surface only requires information obtained from the second Purkinje images or reflections as long as the shape of the anterior surface is already available. Referring to FIG. 7, this means that first Purkinje image 1 is not needed for constructing the model representing the posterior surface of the cornea. The coordinates of a point on the posterior surface can e.g. be determined by the following numerical procedure. The paths 3-5,5-9,9-10,10-2 can be represented by 4 vectors which will form 12 scalar equations. The model of the anterior and posterior surface forms 3 equations corresponding to points 5, 9 and 10. Two refraction events at the anterior surface will form 2 vector (6 scalar) equations obeying Snell's Law. Finally, four equations can be set-up for the reflection event at the posterior surface: 3 equations coming from the cross product reflection principle and 1 equation coming from the inner product reflection principle. All in all, these are 25 equations which are needed to determine 25 unknowns: coordinates of points 5,9, and 10 (9 unknowns), lengths (4 unknowns) and directional cosines (12 unknowns) of the 4 ray vectors. Using standard techniques, the 25 unknowns are solved using the 25 equations.

As the brightness of the first and second Purkinje image is substantially different, this way of determining a model for the posterior surface provides an advantage as in this case, the illumination level of the stimulator point light sources can be set such that the intersection points can accurately be determined, as explained in FIG. 4.

The latter method provides a further advantage in that the camera system of the apparatus according to the present disclosure can be set such that the second Purkinje images are in focus. In this respect, it can be noted that the first and second Purkinje images do not originate from the same plane and as such, an image comprising the first and second Purkinje images cannot have both types of images in focus.

Once the shapes of the anterior and posterior surface is available then the corneal thickness can also be determined.

Regarding the model for the anterior surface, as mentioned, this can either be obtained by known techniques such as the use of a Placido ring topographer or slit imaging systems. When data from the anterior surface is available and when the light source is a collimated beam, the determination of the shape of the posterior surface can also be derived solely from the second Purkinje images. As an example, point 4 in FIG. 6 may thus be traced directly from the source point 3 itself.

As an alternative, a reflected image of the stimulator point light sources as applied in the present method and apparatus to determine the posterior surface, may advantageously be applied to determine the anterior surface. It should be emphasised that either the same image can be applied or an image taken at a different instance. When the same image is used, it will be clear that this provides the advantage that a displacement/movement of the eye does not affect the determination of the corneal thickness. This can be considered an important advantage compared to methods requiring multiple images taken at different instances (e.g. when different illuminator sources are used). The latter case may however also provide an advantage in accurately assessing the coordinates of the light source image on the captured image, as is illustrated in FIG. 4.

In accordance with a second aspect of the present disclosure, there is provided a method and apparatus for determining the shape of the lens of an eye, by means of ray-tracing.

A stimulator light source as described above and an apparatus as e.g. described in FIG. 1 may be applied to determine the shape of the lens. In accordance with the second aspect of the disclosure, this is realised by applying ray-tracing techniques on 3th and 4th Purkinje images that are captured, e.g. by a camera system as described above.

Figure 8:
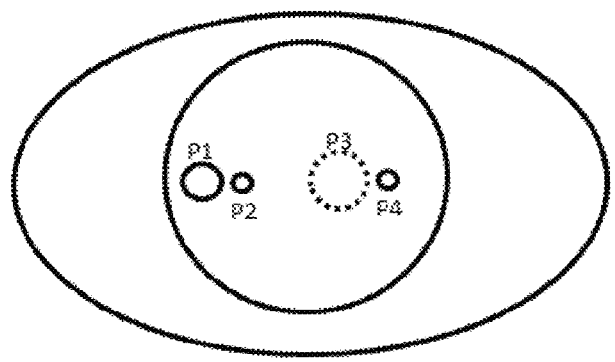
FIG. 8 schematically illustrates first, second, third and fourth Purkinje images originating from a stimulator point light source.

When an eye is illuminated by a stimulator point light source, a reflected image of such point light source will, in addition to the generation of a first and second Purkinje image (caused by reflections from the anterior and posterior surfaces of the cornea), generate a third and fourth Purkinje image which describes a reflection from the front and back surface of the lens of the eye. FIG. 8 schematically shows a relative position of the first, second, third and fourth Purkinje images of a single point light source. FIG. 8 schematically shows Purkinje images caused by a reflection at the anterior corneal surface (P1), at the posterior corneal surface (P2), at the front lens surface (P3) and at the back lens surface (P4). In accordance with the second aspect of the present disclosure, ray-tracing is applied to obtain a model of either the front surface of the lens, based on the third Purkinje images (P3), or the back surface of the lens, based on the fourth Purkinje images (P4) or both.

Figure 9:
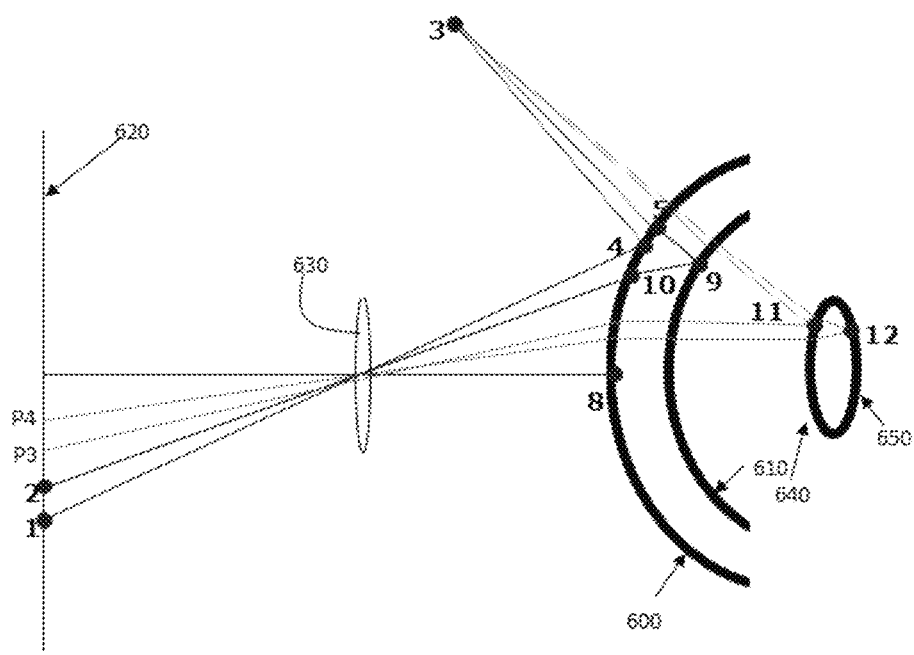
FIG. 9 schematically illustrates an embodiment of the use of ray-tracing to obtain a model of the front surface and/or the back surface of a lens of an eye as applied in the present disclosure.

FIG. 9 schematically illustrates the use of ray-tracing to obtain a model of the front and/or back surface of the lens (having a front surface 640 and a back surface 650) as applied in the present disclosure. As can be seen, point 11 in FIG. 9 represents a point on the front surface 640 of the lens, whereas point 12 represent a point on the back surface 650 of the lens.

FIG. 9 further schematically shows the generation of the first and second Purkinje images (1 and 2 in FIG. 9) and corresponding rays, in a similar manner as shown in FIG. 7, including the anterior 600 and posterior 610 surfaces of the cornea, a stimulator point light source 3, a ray of light 3-4 originating from a stimulator point light source and the reflected rays of said ray of light on both the anterior and posterior surfaces 600, 610, said reflected rays being captured by a camera system 620. FIG. 9 further shows a lens 630 representing a nodal point of the camera system 620.

As can be derived from FIG. 9, a shape of the front surface (640) of the lens (point 11 being one point on the front surface) can be reconstructed based on the locations of the third Purkinje images (P3) as captured on a camera system 620, when the eye is illuminated by a plurality of stimulator point light sources, e.g. a light source as described in FIG. 3.

Further, a shape of the back surface (650) of the lens (point 12 being one point on the back surface) can be reconstructed or modelled based on the locations of the fourth Purkinje images (P4).

Note that, as can be seen from FIG. 9, the position and shape of the cornea are required to accurately perform the ray-tracing of the third Purkinje images and thus arrive at a point on the front surface of the lens. As such, a model of the cornea is required to perform the ray-tracing process.

As such, in an embodiment of the present disclosure there is provided a method of obtaining a model of the front surface of the lens of an eye, the method comprising the following steps:

illuminating an eye by a plurality of stimulator point light sources, capturing an image of the eye comprising reflected images of the stimulator point light sources, the reflected images including 3th and 4th Purkinje images;

obtaining a model representing an anterior surface of a cornea of the eye, obtaining a model representing a posterior surface of the cornea of the eye, constructing a first model representing a front surface of the lens of the eye from the image by ray-tracing the reflected images of the stimulator point light sources towards the stimulator point light sources via the models representing the anterior and posterior surfaces of the cornea.

Similar ray-tracing techniques as described in FIG. 7 can be applied to determine a position of a point (11) on the front surface of the lens or a point (12) on the back surface of the lens.

The coordinates of a point on the front surface can e.g. be determined by the following numerical procedure. A set of equations can be constructed in a similar manner as described in FIG. 7, taking into account the paths as followed from stimulator point 3, via the point 11 on the front surface 640 of the lens to the third Purkinje image P3, the model of the anterior and posterior surfaces, the refraction events at the anterior surface, forming equations obeying Snell's Law and the reflection event at the front surface of the lens.

This set of equations may be solved using standard techniques. In a similar manner, a set of equations can be derived to determine a position of a point (12) on the back surface of the lens.

In an embodiment, once a set of points 11, i.e. points on the front surface of the lens is determined using the ray-tracing as described, this set of points may be used to approximate the shape of the front surface by means of a mathematical model (which can e.g. be in the form of sum of Zernike polynomials, Taylor series, a toric asphere model or the like, as already discussed above). Similarly, once a set of points 12, i.e. points on the back surface of the lens is determined using the ray-tracing as described, this set of points may be used to approximate the shape of the back surface by means of a mathematical model (which can e.g. be in the form of sum of Zernike polynomials, Taylor series, a toric asphere model or the like, as already discussed above).

In an embodiment, the x,y,z location of the set of points (11) can be determined through a best fit of the model that would be consistent to the tracing of rays between the source points (3) and the captured image (P3) going through a combination of refractions and reflections accordingly. The ray tracing may also be made consistent with the designated refractive indices of the various media (e.g. air, cornea, aqueous, lens) the rays are going through. In such embodiment, the set of points (11) are deemed to fit to the mathematical model as applied. As an example, the set of point (11) may be expressed as to lay on a mathematical model including a weighted sum of a set of Zernike polynomials. As such, the aforementioned set of equations can be solved simultaneously with the boundary condition that the points (11) are to be expressed as the mentioned weighted combination.

In a similar manner, a mathematical model of the back surface of the lens can be determined.

Such an approach to arrive at the mathematical model of the front surface or the back surface results in a more robust mathematical model. This approach has been proved to be less susceptible to errors that may have been caused by outliers in the points 11 or 12, when these points are determined without the boundary condition of being fitted to a particular mathematical model.

As will be apparent to the skilled person, FIG. 9 schematically illustrates that the chief ray of the 3th Purkinje image takes a different path as the chief ray for the 4th Purkinje image. Such a situation may occur (as already discussed above) when non-collimated light sources are used, LEDs or the like.

In such case, the construction of the back surface 640 of the lens only requires information obtained from the 4th Purkinje images or reflections as long as the shape of the front surface 650 is already available. Referring to FIG. 9, this means that 3th Purkinje image 1 is not needed for constructing the model representing the back surface 650 of the lens.

In an embodiment, the method further comprises the step of:

determining a model of the back surface of the lens by means of ray tracing of the 4th Purkinje images as captured on an image towards the image source via the anterior and posterior surface models and the model of the front surface of the lens.

In an embodiment, the anterior and/or posterior models of the cornea are obtained by means of ray-tracing as e.g. described above, i.e. by means or ray-tracing of the first and second Purkinje images as e.g. described in FIGS. 6 and 7.

Figure 10:
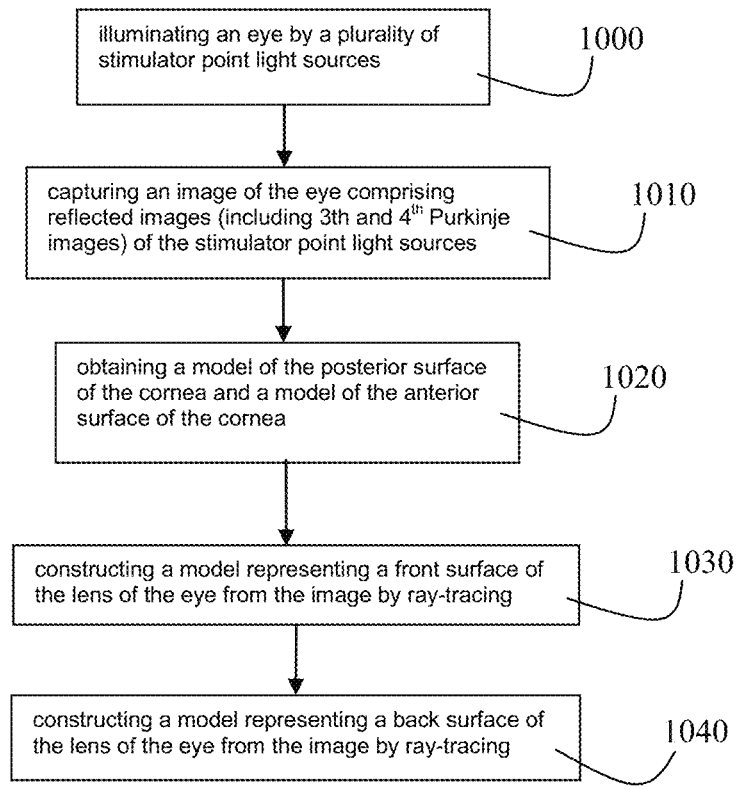
FIG. 10 schematically depicts a flow chart of another embodiment of the method according to the disclosure.

The flow chart of FIG. 10 schematically shows the steps of some embodiments of the method to arrive at a model for the lens of an eye.

In a first step 1000, an eye is illuminated by stimulator point light sources, e.g. a plurality of LEDs or laser beams.

In a second step 1010, an image of the eye is captured (e.g. by means of a camera system such as a 2-dimensional CCD camera), the image including 3th and 4th Purkinje images.

In a third step 1020, models for the anterior and posterior surface of the cornea of the eye are obtained. These may e.g. be obtained from other measurements using other equipment or may be obtained by ray-tracing methods as described above.

In a fourth step 1030, ray-tracing is applied to obtain a model of the front surface of the lens of the eye. This step makes use of the corneal models as obtained in step 1020.

Optionally, in a fifth step 1040, ray-tracing is applied to obtain a model of the back surface of the lens of the eye as well, this step including the use of the model of the front surface of the lens, as explained above.

When both the front and back surface of the lens are modelled, the lens shape, including the lens thickness, can be reconstructed or modelled.

As such, the methods according to the second aspect of the disclosure, enable the shape of the front surface of the lens to be reconstructed or modelled using the location of the captured 3th Purkinje images in combination with the anterior and posterior models of the cornea (whereby the anterior and/or posterior models of the cornea may be obtained using information from 1st and 2nd Purkinje images). In a similar manner, when the shape of the front surface (640) of the lens is known, the back surface (650) of the lens can be reconstructed through determination of the location of a set of points (12) via a fitting routine of tracing rays between a set of points P4 (4th Purkinje images) and the stimulator point sources (3).

The methods as described in FIGS. 9 and 10 may be executed by means of an apparatus for eye analysis. Therefore, in an embodiment, the present disclosure provides in an apparatus for eye analysis, the apparatus comprising
- a plurality of stimulator point light sources for, in use, illuminating an eye,
- a camera system for capturing reflected images of the stimulator point light sources, the reflected images including 3th and 4th Purkinje images;
- a computational unit configured to, in use, perform the following steps:
  - obtaining a first model representing an anterior surface of the cornea of the eye
  - obtaining a model representing a posterior surface of the cornea of the eye,
  - constructing a first model representing a front surface of a lens of the eye from the image by ray-tracing the reflected images of the stimulator point light sources towards the stimulator point light sources via the models representing the anterior and posterior surfaces of the cornea.

The apparatus as described in FIG. 1 may e.g. be configured as an apparatus for eye analysis, whereby the computational unit 150 is configured to perform the indicated steps and wherein the camera system 120 is performed to capture the required reflected images.

As the focal plane of P3 is farthest among the Purkinje images (P1, P2, P3 and P4), additional optical elements (or a second camera at a different distance from the node) may be used to better resolve the position of P3. Such elements may include but are not limited to: a flip mirror to divert the image along a longer optical path to a single camera; or a semi-reflective beam-splitting prism to overlap both optical paths.

Figure 11:
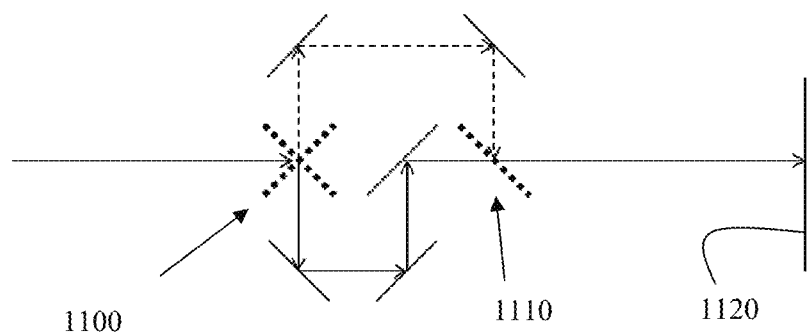
FIG. 11 schematically depicts a flip mirror arrangement as can be applied in a camera system of an apparatus according to the present disclosure.

FIG. 11 schematically shows the mentioned arrangement including a pair of flip mirrors 1100 and 1110 to increase the length of a Path 2 relative to a Path 1 towards a camera 1120. Using such a flip mirror arrangement, reflected images that are to be received by the camera system (the reflected images including the aforementioned Purkinje images), can be alternatingly directed along a first and a second optical path, the first and second optical path having a different length.

Figure 12:
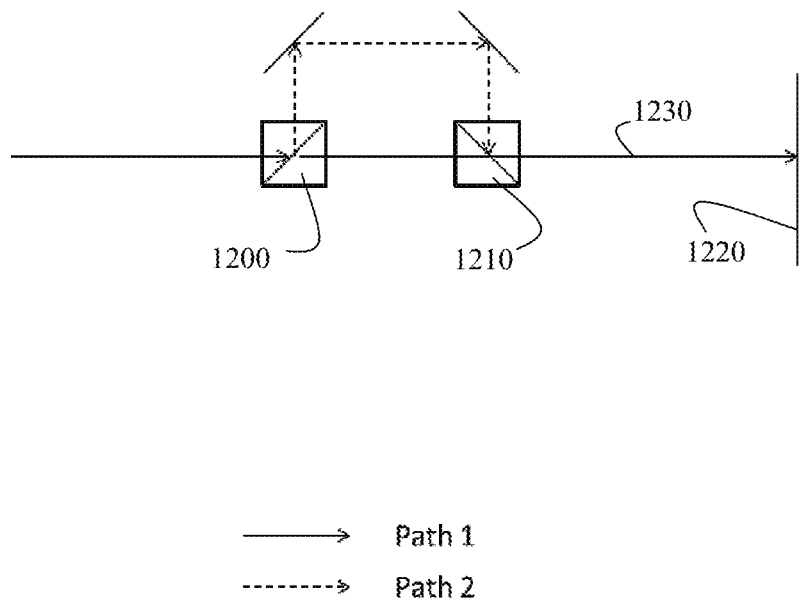
FIG. 12 schematically depicts a beam splitter arrangement as can be applied in a camera system of an apparatus according to the present disclosure.

FIG. 12 schematically shows the mentioned arrangement including a pair of semi-reflective beam-splitting prisms or cubes 1200 and 1210, ensuring that both optical paths (Path 1 and Path 2, the paths having a different optical path length), overlap and arrive at the same position on the same camera 1220. As such, using such a beam-splitting arrangement, reflected images can be directed along a first and a second optical path, the first and second optical path having a different length, whereby a final part, e.g. part 1230 as shown in FIG. 12, of the first optical path coinciding with a final part of the second optical path.

In accordance with a third aspect of the present disclosure, there is provided a method and apparatus to obtain an optical model of eye. Using such a model, by means of ray-tracing, the refractive properties of the eye as a whole can be modelled and determined. The optical model includes models of the anterior and posterior corneal surfaces, the central corneal thickness, the anterior chamber depth, models for the front and back surfaces of the lens and the lens thickness. Using the model, refractive properties such as spherical error, cylindrical error and optical aberrations may be determined for the whole eye as well as the total spherical power, total cylinder and total corneal aberrations.

The refraction properties of an eye can be determined based on the combined information of the shapes of the anterior and posterior corneal surfaces, the shapes of the front and back lenticular surfaces (i.e. the front and back surfaces of the lens of the eye), the thicknesses of the cornea and the lens as well as the anterior chamber depth.

As described in detail above, based on reflections of the first for fourth Purkinje images, the following parameters that are relevant for an optical model of an eye can be retrieved: the shapes of the anterior and posterior corneal surfaces (e.g. using the first and second Purkinje images), the shapes of the front and back lenticular surfaces, the thicknesses of the cornea and the lens as well as the anterior chamber depth.

Therefore, in an embodiment, the method comprises the steps of:
- illuminating an eye by a plurality of stimulator point light sources,
- capturing one or more images of the eye comprising reflected images of the stimulator point light sources,
- constructing a first model representing an anterior surface of the cornea of the eye by ray-tracing the reflected images of the stimulator point light sources towards the stimulator point light sources, the reflected images including 1st Purkinje images of the stimulator point light sources;
- constructing a second model representing a posterior surface of the cornea by ray-tracing the reflected images of the stimulator point light sources via the model representing the anterior surface of the cornea, towards the stimulator point light sources, the reflected images including 2nd Purkinje images of the stimulator point light sources;
- constructing a third model representing a front surface of the lens of the eye by ray-tracing the reflected images of the stimulator point light sources towards the stimulator point light sources via the models representing the anterior and posterior surfaces of the cornea, the reflected images including 3th Purkinje images of the stimulator point light sources;
- constructing a fourth model representing a back surface of the lens of the eye by ray-tracing the reflected images of the stimulator point light sources towards the stimulator point light sources via the models representing the anterior and posterior surfaces of the cornea and the third model representing the front surface of the lens, the reflected images including 4th Purkinje images of the stimulator point light sources;
- determining a central corneal thickness based on the first and second model;
- determining a thickness of the lens of the eye based on the third and fourth model and
- determining an anterior chamber depth.

The method according to the present disclosure to determine an optical model of the eye thus makes use of ray-tracing to construct four models representing the front and back surfaces of both the cornea and the lens of the eye. As can be seen, use is made of the different Purkinje images as described above. The construction of the four models can be based on a single image, the image including the 1st, 2nd, 3th and 4th Purkinje images or it can be based on the use of more than one image, thus enabling an optimal configuration of the stimulator point light sources for determining a particular model or models. In this respect, reference can e.g. be made to FIG. 4 indicating that setting the appropriate intensity of the stimulator point light sources enables a more accurate determination of the location of a Purkinje image on a captured image.

The optical model as determined also includes, as a parameter, the anterior chamber depth which is usually defined as the distance between the front surface of the cornea to the front surface of the lens.

In an embodiment, this parameter is determined based on the positions of the different models associated with the cornea and the lens, as determined using the ray-tracing.

As an alternative, the anterior chamber depth may also be determined based on additional measurements, e.g. by means of a slit lamp or optical coherence tomography using low coherence interferometry.

In an embodiment, the method further includes obtaining a value of an axial length of the eye or perform a measurement, e.g. using low coherence tomography, for obtaining the axial length of the eye.

Based on the model as derived, refractive properties of the total eye, including refractive aberrations can be determined.

This can e.g. be done by ray-tracing a bundle of rays through the optical model of the eye. The cylindrical error as well as the refractive aberrations can be derived from the wavefront data resulting from the difference of optical path length of rays (ex. peripheral ray) compared to the optical path length of the ray passing through the optical axis.

Figure 13:
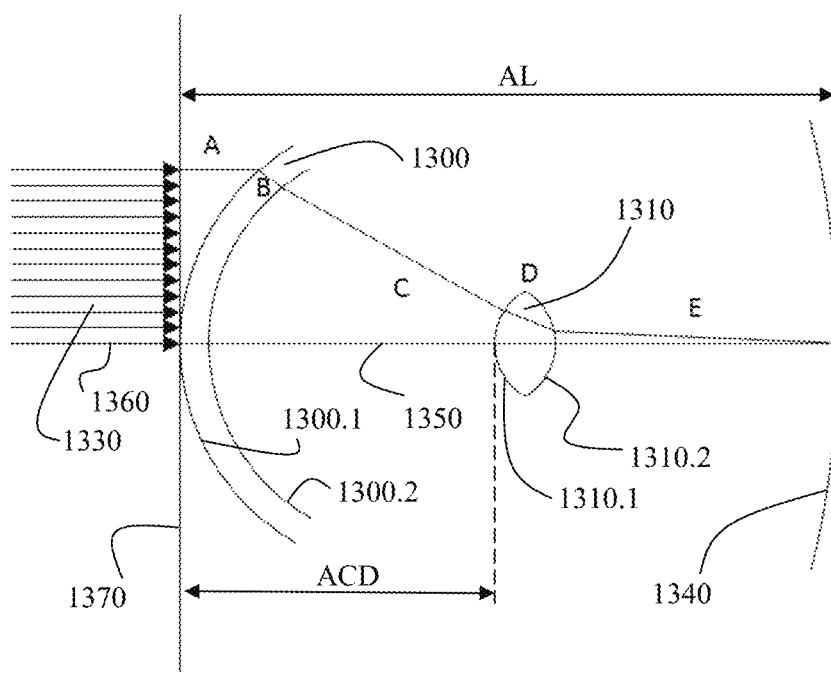
FIG. 13 schematically depicts and optical model of an eye as can be obtained by an embodiment of the method according to the disclosure.

The ray-tracing is schematically shown in FIG. 13. FIG. 13 schematically shows an embodiment of the optical model of the eye as obtained by the method according to the present disclosure, the model including the cornea 1300 (having an anterior surface 1300.1 and a posterior surface 1300.2) and the lens 1310 (having an front surface 1310.1 and a back surface 1310.2), appropriately positioned relative to each other according to the anterior chamber depth ACD. FIG. 13 further indicates the axial eye length AL, being the distance between the front surface of the cornea 1300.1 and the retina 1340.

FIG. 13 also shows a bundle of rays 1330 which can be propagated through the optical model by means of ray-tracing. When doing so, one may e.g. notice that the focal point of the rays need not necessarily be coinciding with the location of the retina 1340. Such a distance discrepancy provides an indication of a defocus error of the eye. By means of the ray-tracing, the cylindrical error as well as the refractive aberrations of the eye can be derived from the wavefront data (i.e. the data obtained by ray-tracing the bundle of rays 1330 through the model) resulting from the difference of optical path length of the various rays. As an example, FIG. 13 schematically shows the propagation of a peripheral ray via paths A,B,C,D and E to the retina) which can be compared to the optical path length of a ray 1360 passing through the optical axis 1350.

Alternatively, or in addition, the ray-tracing procedure can also be started at the retina 1340, where a bundle of rays of varying angles with respect to the optical axis 1350 can be traced until the corneal apex plane 1370 or any reference plane of interest to determine any wavefront aberrations of the eye which will already include defocus.

The method to obtain the optical model of the eye as described above, may be performed by an apparatus for eye analysis according to the present disclosure. Such an apparatus including:
  a plurality of stimulator point light sources for, in use, illuminating an eye,
  a camera system configured to capture one or more images of the eye comprising reflected images of the stimulator point light sources;
  a computational unit configured to, in use, perform the following steps:
    constructing a first model representing an anterior surface of the cornea of the eye by ray-tracing the reflected images of the stimulator point light sources towards the stimulator point light sources, the reflected images including 1st Purkinje images of the stimulator point light sources;
    constructing a second model representing a posterior surface of the cornea by ray-tracing the reflected images of the stimulator point light sources via the model representing the anterior surface of the cornea, towards the stimulator point light sources, the reflected images including 2nd Purkinje images of the stimulator point light sources;
    constructing a third model representing a front surface of the lens of the eye by ray-tracing the reflected images of the stimulator point light sources towards the stimulator point light sources via the models representing the anterior and posterior surfaces of the cornea, the reflected images including 3th Purkinje images of the stimulator point light sources;
    constructing a fourth model representing a back surface of the lens of the eye by ray-tracing the reflected images of the stimulator point light sources towards the stimulator point light sources via the models representing the anterior and posterior surfaces of the cornea and the third model representing the front surface of the lens, the reflected images including 4th Purkinje images of the stimulator point light sources;
    determining a central corneal thickness based on the first and second model;
    determining a thickness of the lens of the eye based on the third and fourth model and
    determining an anterior chamber depth of the eye.

The apparatus as described in FIG. 1 may e.g. be configured as such an apparatus for eye analysis, whereby the computational unit 150 is configured to perform the indicated steps and wherein the camera system 120 is performed to capture the required reflected images.

It should also be noted that 'light' within the meaning of the present disclosure is not limited to visible light, in a preferred embodiment, the stimulator point light sources provide IR light.

As required, detailed embodiments of the present disclosure are disclosed herein; however, it is to be understood that the disclosed embodiments are merely exemplary of the disclosure, which can be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Further, the terms and phrases used herein are not intended to be limiting, but rather, to provide an understandable description of the disclosure.

The terms "a" or "an", as used herein, are defined as one or more than one. The term plurality, as used herein, is defined as two or more than two. The term another, as used herein, is defined as at least a second or more. The terms including and/or having, as used herein, are defined as comprising (i.e., open language, not excluding other elements or steps). Any reference signs in the claims should not be construed as limiting the scope of the claims or the disclosure.

The mere fact that certain measures are recited in mutually different dependent claims does not indicate that a combination of these measures cannot be used to advantage.

The term coupled, as used herein, is defined as connected, although not necessarily directly, and not necessarily mechanically.

We claim:

1. A method of determining a model of a lens of an eye, the method comprising the steps of:
   illuminating an eye by a plurality of stimulator point light sources;
   capturing an image of the eye comprising reflected images of the stimulator point light sources, the reflected images including 3th and 4th Purkinje images;
   obtaining a first model representing an anterior surface of a cornea of the eye;
   obtaining a second model representing a posterior surface of the cornea of the eye; and
   constructing a third model representing a front surface of the lens of the eye from the image by ray-tracing the reflected images of the stimulator point light sources towards the stimulator point light sources via the first and second models representing the anterior and posterior surfaces of the cornea.

2. The method according to claim 1, further comprising the step of:
   constructing a second model representing a back surface of the lens of the eye from the image by ray-tracing the reflected images of the stimulator point light sources towards the stimulator point light sources via the first and second models representing the anterior and posterior surfaces of the cornea and the third model representing the front surface of the lens.

3. The method according to claim 1, wherein the reflected images of the stimulator point light sources further comprise first and second Purkinje images, and wherein the step of obtaining a second model representing a posterior surface of the cornea of the eye comprises:
   constructing the second model representing the posterior surface of the cornea from the image by ray-tracing the reflected images of the stimulator point light sources towards the first model representing the anterior surface of the cornea.

4. The method according to claim 1, wherein the step of obtaining a second model representing a posterior surface of the cornea of the eye comprises:
   capturing an image of the cornea comprising reflected images of the stimulator point light sources, the reflected images of the stimulator point light sources comprise first and second Purkinje images; and
   constructing the second model representing the posterior surface of the cornea from the image by ray-tracing the reflected images of the stimulator point light sources towards the first model representing the anterior surface of the cornea.

5. The method according to claim 1, wherein the first model of the anterior surface of the cornea is determined using a corneal topographer.

6. The method according to claim 1, wherein the first model representing the anterior surface of the cornea is obtained by:
   capturing a corneal image obtained by illuminating the cornea with a stimulator source;
   using ray-tracing to determine a point of reflection of the stimulator source on the anterior surface; and
   performing a fitting algorithm of the point of reflection to a mathematical model to obtain the first model representing the anterior surface of the cornea.

7. The method according to claim 6, wherein the image of the cornea is used as the corneal image.

8. The method according to claim 7, wherein the corneal image is obtained by illuminating the cornea by the plurality of stimulator point light sources with a lower illumination level as the image of the cornea.

9. The method according to claim 1, wherein the first model representing the anterior surface comprises one of a plurality of Zernike polynomials, and a toric aspheric model.

10. Apparatus for eye analysis comprising:
    a plurality of stimulator point light sources for, in use, illuminating an eye;
    a camera system configured to capture reflected images of the stimulator point light sources, the reflected images including 3th and 4th Purkinje images; and
    a computational unit configured to, in use, perform the following steps:
       obtaining a first model representing an anterior surface of the cornea of the eye;
       obtaining a second model representing a posterior surface of the cornea of the eye; and
       constructing a third model representing a front surface of a lens of the eye from the image by ray-tracing the reflected images of the stimulator point light sources towards the stimulator point light sources via the first and second models representing the anterior and posterior surfaces of the cornea.

11. The apparatus according to claim 10, wherein the computational unit is further configured to perform the step of constructing a second model representing a back surface of the lens of the eye from the image by ray-tracing the reflected images of the stimulator point light sources towards the stimulator point light sources via the first and second models representing the anterior and posterior surfaces of the cornea and the third model representing the front surface of the lens of the eye.

12. The apparatus according to claim 10, wherein the computational unit is configured to, in use, perform the step of obtaining a second model representing a posterior surface of the cornea of the eye by constructing a second model representing the posterior surface of the cornea by ray-tracing the reflected images of the stimulator point light sources towards the first model representing the anterior surface of the cornea.

13. The apparatus according to claim 10, wherein the computational unit is configured to, in use, perform the step of determining a corneal thickness from the first model representing the anterior surface and the second model representing the posterior surface.

14. The apparatus according to claim 10, further comprising a flip mirror arrangement configured to alternatingly direct the reflected images along a first and a second optical path, the first and second optical path having a different length.

15. The apparatus according to claim 10, further comprising a beam-splitting arrangement configured to direct the reflected images along a first and a second optical path, the first and second optical path having a different length and a final part of the first optical path coinciding with a final part of the second optical path.

16. The apparatus according to claim 15, wherein the beam-splitting arrangement comprises a pair of semi-reflective beam-splitting prisms.

17. The apparatus according to claim 10, further comprising a control unit for setting an illumination level of the stimulator point light sources.

18. The apparatus according to claim 17, wherein the control unit is further arranged to selectively enable the stimulator point light sources.

19. The apparatus according to claim 10, wherein the stimulator point light sources comprise an LED or a laser diode.

20. The apparatus according to claim 10, wherein the stimulator point light sources originate from a collimated light source.

21. The apparatus according to claim 10, wherein the plurality of stimulator point light sources are distributed along one or more concentric circles.

22. The apparatus according to claim 21, wherein each circle comprises an evenly distributed odd number of stimulator point light sources.

23. The apparatus according to claim 21, wherein the stimulator point light sources are not diametrically opposed.

24. A method of determining an optical model of an eye, the method comprising the steps of:
    illuminating an eye by a plurality of stimulator point light sources;
    capturing one or more images of the eye comprising reflected images of the stimulator point light sources,
    constructing a first model representing an anterior surface of the cornea of the eye by ray-tracing the reflected images of the stimulator point light sources towards the stimulator point light sources, the reflected images including 1st Purkinje images of the stimulator point light sources;
    constructing a second model representing a posterior surface of the cornea by ray-tracing the reflected images of the stimulator point light sources via the first model representing the anterior surface of the cornea, towards the stimulator point light sources, the reflected images including 2nd Purkinje images of the stimulator point light sources;
    constructing a third model representing a front surface of the lens of the eye by ray-tracing the reflected images of the stimulator point light sources towards the stimulator point light sources via the first and second models representing the anterior and posterior surfaces of the cornea, the reflected images including 3th Purkinje images of the stimulator point light sources;
    constructing a fourth model representing a back surface of the lens of the eye by ray-tracing the reflected images of the stimulator point light sources towards the stimulator point light sources via the first and second models representing the anterior and posterior surfaces of the cornea and the third model representing the front surface of the lens, the reflected images including 4th Purkinje images of the stimulator point light sources;
    determining a central corneal thickness based on the first and second models;
    determining a thickness of the lens of the eye based on the third and fourth models; and
    determining an anterior chamber depth.

25. The method according to claim 24, wherein the anterior chamber depth is determined by means of slit lamp measurements or optical coherence tomography using low coherence interferometry.

26. The method according to claim 24, further comprising the step of obtaining an axial length of the eye.

27. The method according to claim 26, wherein the axial length of the eye is obtained by means of low coherence tomography.

28. Apparatus for eye analysis comprising:
    a plurality of stimulator point light sources for, in use, illuminating an eye;
    a camera system configured to capture one or more images of the eye comprising reflected images of the stimulator point light sources; and
    a computational unit configured to, in use, perform the following steps:
        constructing a first model representing an anterior surface of the cornea of the eye by ray-tracing the reflected images of the stimulator point light sources towards the stimulator point light sources, the reflected images including 1st Purkinje images of the stimulator point light sources;
        constructing a second model representing a posterior surface of the cornea by ray-tracing the reflected images of the stimulator point light sources via the first model representing the anterior surface of the cornea, towards the stimulator point light sources, the reflected images including 2nd Purkinje images of the stimulator point light sources;
        constructing a third model representing a front surface of the lens of the eye by ray-tracing the reflected images of the stimulator point light sources towards the stimulator point light sources via the first and second models representing the anterior and posterior surfaces of the cornea, the reflected images including 3th Purkinje images of the stimulator point light sources;
        constructing a fourth model representing a back surface of the lens of the eye by ray-tracing the reflected images of the stimulator point light sources towards the stimulator point light sources via the first and second models representing the anterior and posterior surfaces of the cornea and the third model representing the front surface of the lens, the reflected images including 4th Purkinje images of the stimulator point light sources;
        determining a central corneal thickness based on the first and second model;
        determining a thickness of the lens of the eye based on the third and fourth model and;
        determining an anterior chamber depth of the eye.

* * * * *